United States Patent [19]

Coenders et al.

[11] Patent Number: 6,130,257
[45] Date of Patent: Oct. 10, 2000

[54] COMPOSITIONS OF ENANTIOMERIC DIACYL TARTARIC ANHYDRIDES AND PREPARATION THEREOF

[75] Inventors: Peter Joannes Coenders, Dordrecht; Saskia Alexandra Galema, Vlaardingen; Johannes Durk Gombert, Velp; Anna Sophie E ter Meer, Vlaardingen, all of Netherlands

[73] Assignee: Quest International B.V., Naarden, Netherlands

[21] Appl. No.: 08/930,088

[22] PCT Filed: May 6, 1996

[86] PCT No.: PCT/EP96/01934

§ 371 Date: Nov. 12, 1997

§ 102(e) Date: Nov. 12, 1997

[87] PCT Pub. No.: WO96/35658

PCT Pub. Date: Nov. 14, 1996

[30] Foreign Application Priority Data

May 12, 1995 [EP] European Pat. Off. .............. 95201233

[51] Int. Cl.$^7$ ........................... B01F 17/36; C07D 307/56
[52] U.S. Cl. .......................... 516/73; 549/253; 549/233; 562/888
[58] Field of Search ..................... 549/233, 253; 252/351, 356; 554/161, 163, 164, 169, 174; 516/73, 75; 560/1; 562/401, 887, 888

[56] References Cited

U.S. PATENT DOCUMENTS

| | | | |
|---|---|---|---|
| 2,628,238 | 2/1953 | Patrick | 549/252 |
| 3,141,013 | 7/1964 | O'Boyle | 554/205 |
| 5,451,687 | 9/1995 | Sato et al. | 549/253 |
| 5,473,103 | 12/1995 | Domb et al. | 562/509 |

FOREIGN PATENT DOCUMENTS

| | | |
|---|---|---|
| 600 714 A1 | 6/1994 | European Pat. Off. . |
| 117065 | 12/1975 | Germany . |

OTHER PUBLICATIONS

Database WPI on WEST, Week 197610, London: Derwent Publications Ltd., AN 1976–17031x, Class D13, DD 117065 A (Stokov I) abstract.

Database WPI on WEST, week 198009, London: Derwent Publications Ltd., AN 1980–16000C, Class D11, SU 654605 A (Mosc Fats Res Inst) abstract.

The Merck Index, An Encyclopedia of Chemicals, Drugs, and Biologicals, Tenth Edition (Merck & Co., Rahway, NJ, 1983) pp. 1302–1303, Jan. 1984.

Villemin et al., "Clay Catalysis: a Convenient and Rapid Formation of Anhydride from Carboxylic Acid and Isopropenyl Acetate under Microwave Irradiation" Synthetic Communications, 23(4), 419–424 (1993).

*Primary Examiner*—Richard D. Lovering
*Assistant Examiner*—Daniel S. Metzmaier
*Attorney, Agent, or Firm*—Pillsbury Madison & Sutro LLP

[57] ABSTRACT

The present invention relates to compositions comprising mixtures of two enantiomeric forms of diacyl tartaric anhydride and mixtures obtainable by reacting an organic compound with a mixture comprising two enantiomeric forms of diacyl tartaric anhydride. The invention also relates to a method for the preparation of such enantiomeric mixtures, starting from a mixture comprising D-tartaric acid and L-tartaric acid. The method involves reacting tartaric acid with a fatty acid anhydride under dielectric heating conditions.

4 Claims, No Drawings ically active, and the meso-form, which is not optical
COMPOSITIONS OF ENANTIOMERIC DIACYL TARTARIC ANHYDRIDES AND PREPARATION THEREOF This application is the national phase of international application PCT/EP96/01934, filed May 6,1996 which designated the U.S.

FIELD OF THE INVENTION

The present invention relates to compositions comprising mixtures of two enantiomeric forms of diacyl tartaric anhydride and mixtures obtainable by reacting an organic compound with a mixture comprising two enantiomeric forms of diacyl tartaric anhydride. The invention also relates to a method for the preparation of such enantiomeric mixtures, starting from a mixture comprising D-tartaric acid and L-tartaric acid.

DESCRIPTION OF RELATED ART

Diacyl tartaric anhydride compounds (such as diacetyl tartaric anhydride, herein after referred to as "DATA"), are versatile chemical intermediates. Such compounds can be used, inter alia, for the manufacture of a large group of emulsifiers for food use, for example by reacting DATA with a fatty acid monoglyceride ester or the corresponding diester or any mixture thereof.

Diacyl tartaric anhydride compounds are generally prepared by reacting tartaric acid with a fatty acid anhydride (having preferably between 1 to 4 carbon atoms). Tartaric acid exists in three basic structures: L-(+)-tartaric acid (natural tartaric acid) and D-(−)-tartaric acid, which are both optical active, and the meso-form, which is not optical active. Mixtures of these forms also exist, e.g. the racemic mixture D,L-tartaric acid. Tartaric acid is a white solid material (at ambient conditions).

At present, diacetyl tartaric anhydride (DATA) is prepared by reacting tartaric acid with acetic anhydride. Both L-tartaric acid, D-tartaric acid as well as D,L-tartaric acid are not well soluble in acetic anhydride. However, once L-tartaric acid starts to react, it is solubilized in acetic anhydride very quickly. On the other hand, D-tartaric acid and D,L-tartaric acid are not well solubilized. For this reason, DATA is prepared up till now starting from L-(+)-tartaric acid, and consequently, diacetyl-L-tartaric anhydride (L-DATA) is obtained.

SUMMARY OF THE INVENTION

Thus, in the conventional reactions for the preparation of diacyl tartaric anhydride starting from tartaric acid and a fatty acid anhydride (having preferably between 1 to 4 carbon atoms), D-tartaric acid and D,L-tartaric acid (the racemic mixture) cannot be used. This is a disadvantage, since it limits the choice of starting materials. Additionally, when L-DATA is used in the preparation of emulsifiers for application of foodstuffs (as set out above), such emulsifiers can generally not be used in applications where all food products and ingredients need to be kosher. Therefore, there is a need for a process in which it would be possible to prepare diacyl tartaric anhydrides by reacting tartaric acid with fatty acid anhydrides (having preferably between 1 to 4 carbon atoms), and wherein it is possible to use equally well L-tartaric acid, D-tartaric acid as well as all mixtures thereof, such as racemic mixtures.

It has now been found that such a process is possible, when at least a part of the reaction between tartaric acid and a fatty acid anhydride (having preferably between 1 and 4 carbon atoms) is carried out under dielectric heating conditions. Preferably, at least the first part of the reaction should be carried out under dielectric heating conditions, and more preferably dielectric heating conditions should be employed during the entire reaction time. As an alternative, the dielectric heating may be employed intermittently.

In Synthetic Communications, 23(4), 419–424 (1993), it is reported that organic reactions can be carried out under dielectric heating (by a microwave). However, its use in connection to the preparation of diacyl tartaric anhydrides is neither mentioned nor suggested, and additionally, its use in connection to reactions involving stereo isomers is also not reported therein.

DESCRIPTION OF PREFERRED EMBODIMENTS

A preferred fatty acid anhydride for the above purpose is acetic anhydride, yielding upon reaction with tartaric acid diacetyl tartaric anhydride (DATA).

It is possible to prepare compositions comprising diacyl tartaric anhydride, which diacyl tartaric anhydride is a mixture of L-diacyl tartaric anhydride and D-diacyl tartaric anhydride, in any desired ratio, depending upon the starting ratio of the L-tartaric acid and D-tartaric acid. As a consequence of this invention, it is now possible to prepare a composition comprising diacyl-L-tartaric anhydride and diacyl-D-tartaric anhydride, wherein the molar ratio of said forms of tartaric anhydride in the composition is between 1:100 and 100:1. For example, the obtained ratio between L-diacyl tartaric anhydride and D-diacyl tartaric anhydride can be any ratio between 1:20 and 20:1. Likewise, the ratio can be around 1:1, as is the case in a racemic mixture.

The compositions according to the above comprising one or more enantiomers of diacyl tartaric anhydride can be used as a starting material in further reactions. Accordingly, compositions are obtainable by reacting:

i. an organic compound, with
ii. a mixture comprising diacyl-L-tartaric anhydride and diacyl-D-tartaric anhydride, wherein the molar ratio of the enantiomers obtained by said reaction of the organic compound (i) with said tartaric anhydrides (ii) is between 1:100 and 100:1, depending on the molar ratio of L- and D-tartaric acid in the starting mixture. Such compositions are also subject of the invention, as well as methods for the preparation of such compositions. Likewise, the obtained ratio can be any ratio between 1:20 and 20:1. The ratio can also be around 1:1, as is the case in a racemic mixture. In the latter case, a racemic mixture of L-diacyl tartaric anhydride and D-diacyl tartaric anhydride can be used for said reaction. The organic compound referred to above which can be used in such a reaction can be e.g. an alcohol. Preferred alcohols are e.g. glycerol monoesters or diesters of a fatty acid and any mixture thereof.

The invention is further exemplified by the following example, but should not be interpreted as limiting the invention.

EXAMPLE

In a three-necked flask, the following ingredients were introduced:

27.6 gram (0.18 mmol) tartaric acid
56 ml (0.59 mmol) acetic anhydride
10 µl (180 ppm) $H_2SO_4$ (concentrated, 96–98%, p.a.)
10 grams of glass beads.

Reactions according to the above recipe were carried out using L-tartaric acid as well as D,L-tartaric acid along the following lines.

The three-necked flask was put in a microwave oven. The temperature regulation was carried out through monitoring the temperature via a fiber optic thermometer (by Luxtron), which was connected to a computer, controlling the temperature. The temperature programme employed ensured quick heating up to at least 100° C. (in about 1–2 minutes), whereafter the temperature was maintained between about 100° C. and about 110° C. Reactions were carried out for 15, 30 45 and 60 minutes. After dielectric heating, the volatile compounds were evaporated under reduced pressure. The product obtained was in all cases an off-white crystalline compound. Both NMR and IR analysis indicated that free OH-groups were substantially absent in the product, from which it can be concluded that the conversion was quantitative.

What is claimed is:

1. Method for the preparation of a mixture of diacyl tartaric anhydride compounds which comprises reacting in the absence of an added solvent:
   i. a fatty acid anhydride of an acid having from 1 to 4 carbon atoms,
   ii. a mixture comprising L-tartaric acid and D-tartaric acid, wherein the molar ratio of said forms of tartaric acid is between 1:100 and 100:1, wherein at least part of the reaction is carried out under dielectric heating.

2. Method according to claim 1, wherein said ratio is between 1:20 and 20:1.

3. Method according to claim 1 or 2, wherein the tartaric acid is present in the form of a racemic mixture.

4. Method according to claim 1, wherein the fatty acid anhydride is acetic anhydride.

* * * * *